(12) United States Patent
Silva et al.

(10) Patent No.: US 8,778,679 B2
(45) Date of Patent: Jul. 15, 2014

(54) UMBILICAL CORD LINING STEM CELLS AND METHODS AND MATERIAL FOR ISOLATING AND CULTURING SAME

(71) Applicant: DaVinci Biosciences LLC, Costa Mesa, CA (US)

(72) Inventors: Francisco J. Silva, Tustin, CA (US); Rafael Gonzalez, Placentia, CA (US)

(73) Assignee: DaVinci Biosciences LLC, Costa Mesa, CA (US)

( * ) Notice: Subject to any disclaimer, the term of this patent is extended or adjusted under 35 U.S.C. 154(b) by 0 days.

(21) Appl. No.: 13/668,138

(22) Filed: Nov. 2, 2012

(65) Prior Publication Data

US 2013/0065302 A1    Mar. 14, 2013

Related U.S. Application Data

(63) Continuation of application No. 13/497,497, filed as application No. PCT/US2010/050025 on Sep. 23, 2010, now abandoned.

(60) Provisional application No. 61/245,123, filed on Sep. 23, 2009.

(51) Int. Cl.
    *C12N 5/00*    (2006.01)
(52) U.S. Cl.
    USPC ........................................................ 435/374
(58) Field of Classification Search
    None
    See application file for complete search history.

(56) References Cited

U.S. PATENT DOCUMENTS

| 2005/0054098 A1* | 3/2005 | Mistry et al. | 435/372 |
| 2006/0182724 A1 | 8/2006 | Riordan | |
| 2007/0196918 A1* | 8/2007 | Sayre et al. | 435/366 |
| 2009/0029463 A1 | 1/2009 | Collins | |

FOREIGN PATENT DOCUMENTS

| WO | WO 2006/019357 | 2/2006 |
| WO | WO 2007/046775 | 4/2007 |

OTHER PUBLICATIONS

Lu et al., Human Bone Marrow Mesenchymal Stem Cells Transfected with Human Insulin Genes Can Secrete Inuslin Stably, Annals of Clinical & Laboratory Science, vol. 36, No. 2, pp. 127-136 (2006).*
Gang et al., SSEA-4 identifies mesenchymal stem cells from bone marrow, Blood, Feb. 15, 2007 vol. 109, No. 4, pp. 1743-1751.*
Sotiropoulou et al., Characterization of the Optimal Culture Conditions for Clinical Scale Production of Human Mesenchymal Stem Cells, Stem Cells 2006; 24: 462-471.*
Kermani et al., Characterization and Genetic Manipulation of Human Umbilical Cord Vein Mesenchymal Stem Cells: Potential Application in Cell-Based Gene Therapy, vol. 11, No. 2, 2008.*
Extended European Search Report in EP Application No. 10819470.5, dated Jun. 28, 2013, 11 pages.
PCT International Search Report mailed Jun. 7, 2011, which issued in corresponding International Application No. PCT/US2010/050025.
Alviano et al., "Term amniotic membrane is a high throughput source for multipotent mesenchymal stem cells with the ability to differentiate into endothelial cells in vitro," BMC Development Biology, Feb. 2007, 7(1):11, 14 pages.
Cononi, "Phenotype and Differentiation Potential of Stromal Populations Obtained from Various Zones of Human Umbilical Cord: An Overview," Open Tissue Engineering Regenerative Med J., Dec. 2011, 4(1):6-20.
Gonzalez et al., "An Efficient Approach to Isolation and Characterization of Pre- and Postnatal Umbilical Cord Lining Stem Cells for Clinical Applications," Cell Transplantation, 2010, 19(11):1439-1449.
Jeschke et al., "Umbilical cord lining membrane and wharton's jelly-derived mesenchymal stem cells: The similarities and differences," Open Tissue Engineering Regenerative Med J., 2011, 4(1):21-27.
Kita et al., "Isolation and characterization of mesenchymal stem cells from the sub-amnitoic human umbilical cord lining membrane," Stem Cells and Development, Apr. 2010, 19(4):491-502.
Maurice, S. et al., "Isolation of progenitor cells from cord blood using adhesion matrices" Cytotechnology, 2007, vol. 54, pp. 121-133.

* cited by examiner

*Primary Examiner* — Suzanne M Noakes
*Assistant Examiner* — Stephen Chong
(74) *Attorney, Agent, or Firm* — Fish & Richardson P.C.

(57) ABSTRACT

Human umbilical cord lining stem cells that are capable of differentiating into cells of the mesodermal lineage and ectodermal lineage are described, as well as methods of isolating, expanding, culturing, and cryopreserving such cells.

32 Claims, 3 Drawing Sheets

UMBILICAL CORD LINING STEM CELLS AND METHODS AND MATERIAL FOR ISOLATING AND CULTURING SAME

CROSS-REFERENCE TO RELATED APPLICATIONS

This application is a continuation of U.S. application Ser. No. 13/497,497, filed Mar. 21, 2012, which is a national stage application of PCT/US2010/050025, filed on Sep. 23, 2010, which claims priority to U.S. Application Ser. No. 61/245,123, filed on Sep. 23, 2009. The disclosures of the prior applications are considered part of (and are incorporated by reference in) the disclosure of this application.

TECHNICAL FIELD

This invention relates to umbilical cord lining stem cells (ULSCs) from humans, and more particularly, to methods and materials for isolating, culturing, expanding, and characterizing ULSCs.

SUMMARY

This invention is based on the discovery of a population of cells from the umbilical cord lining, termed umbilical cord lining stem cells (ULSCs) and methods and materials for isolating such cells. ULSCs are positive for cell surface markers CD73, CD90, CD105, CD106, SSEA-4, and STRO-1 and lack hematopoietic cell surface markers CD34, CD45, and HLA-DR. In addition, ULSCs express pluripotent markers Oct4 and Nanog. ULSCs can be propagated for at least 60 population doublings. ULSCs also have a broad plasticity and the ability to differentiate into adipogenic, osteogenic, chondrogenic, neurogenic, and cardiogenic cells. The results described herein demonstrate that ULSCs can be easily obtained and expanded in culture to therapeutically relevant numbers in a short period of time. In addition, ULSCs can be cryopreserved, making the cells suitable for banking of the cells for later therapeutic uses.

In one aspect, this document features a method for isolating ULSCs from an umbilical cord. The method includes obtaining the lining of an umbilical cord, wherein the lining is substantially free of blood, venous tissue, and arterial tissue; and culturing explants of the lining on a fibronectin-coated solid substrate in the presence of a low glucose growth medium for a period of time sufficient for the ULSCs to adhere to the fibronectin-coated solid substrate, wherein the growth medium includes 15% fetal bovine serum, a stabilized dipeptide of L-alanyl-L-glutamine, antibiotic (e.g., gentamycin, or penicillin and streptomycin), and a growth factor selected from the group consisting of basic fibroblast growth factor (bFGF), leukemia inhibitory factor (LIF), and epidermal growth factor (EGF). The growth medium further can include insulin, transferrin, selenium, and sodium pyruvate, and in some embodiments, putrescine. In some embodiments, the growth medium includes bFGF, LIF, and EGF. The upper surface of each explant can be in contact with a solid substrate (e.g., coverslip). The method further can include washing the cells adhered to the fibronectin-coated solid substrate.

In another aspect, this document features a composition for culturing ULSCs. The composition includes a low glucose growth medium; 10% to 20% serum; 0.7 to 1.5% of a stabilized dipeptide of L-alanyl-L-glutamine; 1 to 100 ng/mL of a growth factor selected from the group consisting of bFGF, LIF, and EGF; and 1 to 3% of an antibiotic. The composition further can include 0.1 mg/mL to 100 mg/mL of insulin; 0.1 mg/mL to 100 mg/mL of transferrin; 0.1 µg/mL to 100 µg/mL of selenium; and 0.5 to 1.5% sodium pyruvate. In some embodiments, the composition further includes 0.05 µg/mL to 100 µg/mL of putrescine and 1 ng/mL to 100 ng/mL of EGF. For example, the composition can include 15% serum (e.g, fetal bovine serum or human serum); 1% of the stabilized dipeptide of L-alanyl-L-glutamine; 10 ng/mL of bFGF; 10 ng/mL LIF; 1% of the antibiotic; 10 ng/mL of insulin; 0.55 mg/mL of transferrin; and 0.5 µg/mL of selenium, and optionally, 10 µg/mL of putrescine and 10 ng/mL of EGF.

This document also features a composition that includes a purified population of ULSCs and a culture medium, wherein the culture medium includes a low glucose growth medium; 10% to 20% serum; 0.7 to 1.5% of a stabilized dipeptide of L-alanyl-L-glutamine; 1 to 100 ng/mL of a growth factor selected from the group consisting of bFGF, LIF, and EGF; and 1 to 3% of an antibiotic, wherein the ULSCs are positive for CD105, CD106, CD90, CD73, SSEA-4, and STRO-1, and negative for CD45, CD34, CD19, and HLA-DR. The ULSCs express OCT4 and Nanog, and do not express SOX2. The culture medium further can include 0.1 mg/mL to 100 mg/mL of insulin; 0.1 mg/mL to 100 mg/mL of transferrin; 0.1 µg/mL to 100 µg/mL of selenium; and 0.5 to 1.5% sodium pyruvate, and optionally, 0.05 µg/mL to 100 µg/mL of putrescine and 1 ng/mL to 100 ng/mL of EGF. The composition further can include a cryopreservative.

In another aspect, this document features a purified population of ULSCs, wherein the cells are positive for CD105, CD106, CD90, CD73, SSEA-4, and STRO-1, negative for CD45, CD34, CD19, and HLA-DR, express OCT4 and Nanog, and do not express Sox2. The cells are capable of differentiating into cells of mesodermal lineage (e.g., adipogenic cells, osteogenic cells, chondrogenic, and cardiogenic cells) or ectodermal lineage (e.g., neurogenic cells). In some embodiments, the cells have undergone at least 50, 60, 70, 80, or 90 doublings in culture. The cells can include an exogenous nucleic acid, e.g., an exogenous nucleic acid encoding a polypeptide. The cells can be housed within a scaffold. In some embodiments, the scaffold is biodegradable. A biodegradable scaffold can be composed of collagen.

This document also features a method for culturing a population of ULSCs. The method includes obtaining a population of ULSCs from human umbilical cord, wherein the ULSCs are positive for CD105, CD106, CD90, CD73, SSEA-4, and STRO-1, negative for CD45, CD34, CD19, and HLA-DR, express OCT4 and Nanog, and do not express Sox2; and culturing the cells in the presence of a low glucose growth medium containing 10% to 20% serum; 0.7 to 1.5% of a stabilized dipeptide of L-alanyl-L-glutamine; 1 to 100 ng/mL of a growth factor selected from the group consisting of bFGF, LIF, and EGF; and 1 to 3% of an antibiotic. The low glucose growth medium further can include 0.1 mg/mL to 100 mg/mL of insulin; 0.1 mg/mL to 100 mg/mL of transferrin; 0.1 µg/mL to 100 µg/mL of selenium; and 0.5 to 1.5% sodium pyruvate. In some embodiments, the low glucose growth medium further includes 0.05 µg/mL to 100 µg/mL of putrescine and 1 ng/mL to 100 ng/mL of EGF.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

Like reference symbols in the various drawings indicate like elements.

DETAILED DESCRIPTION

Figure 1:
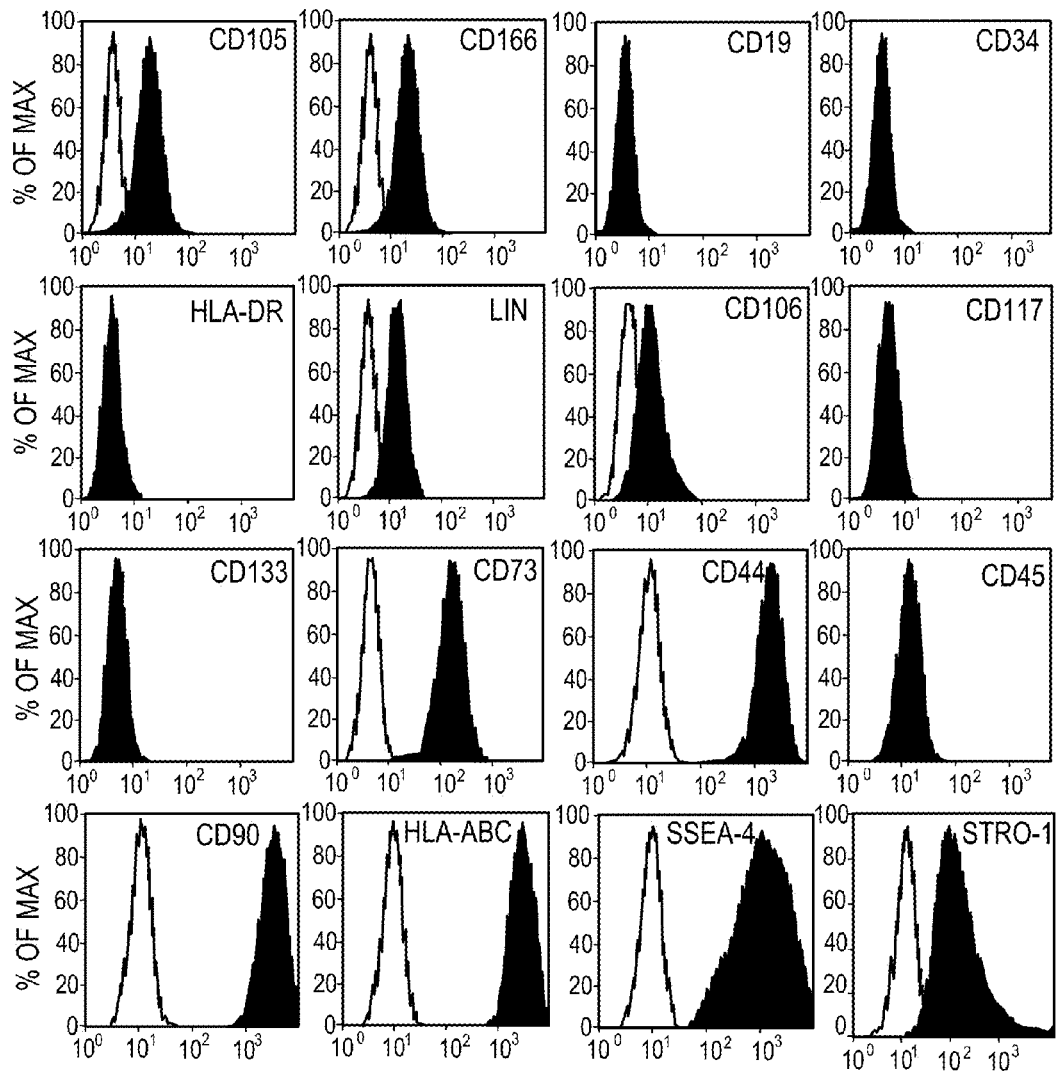
FIG. 1 contains histograms of prenatal (left panels) or adult (right panels) ULSCs subjected to FACS for the cell surface markers CD105, CD166, CD19, CD34, HLA-DR, LIN, CD106, CD117, CD133, CD73, CD44, CD45, CD90, HLA-ABC, SSEA-4, and STRO-1.
Figure 1:
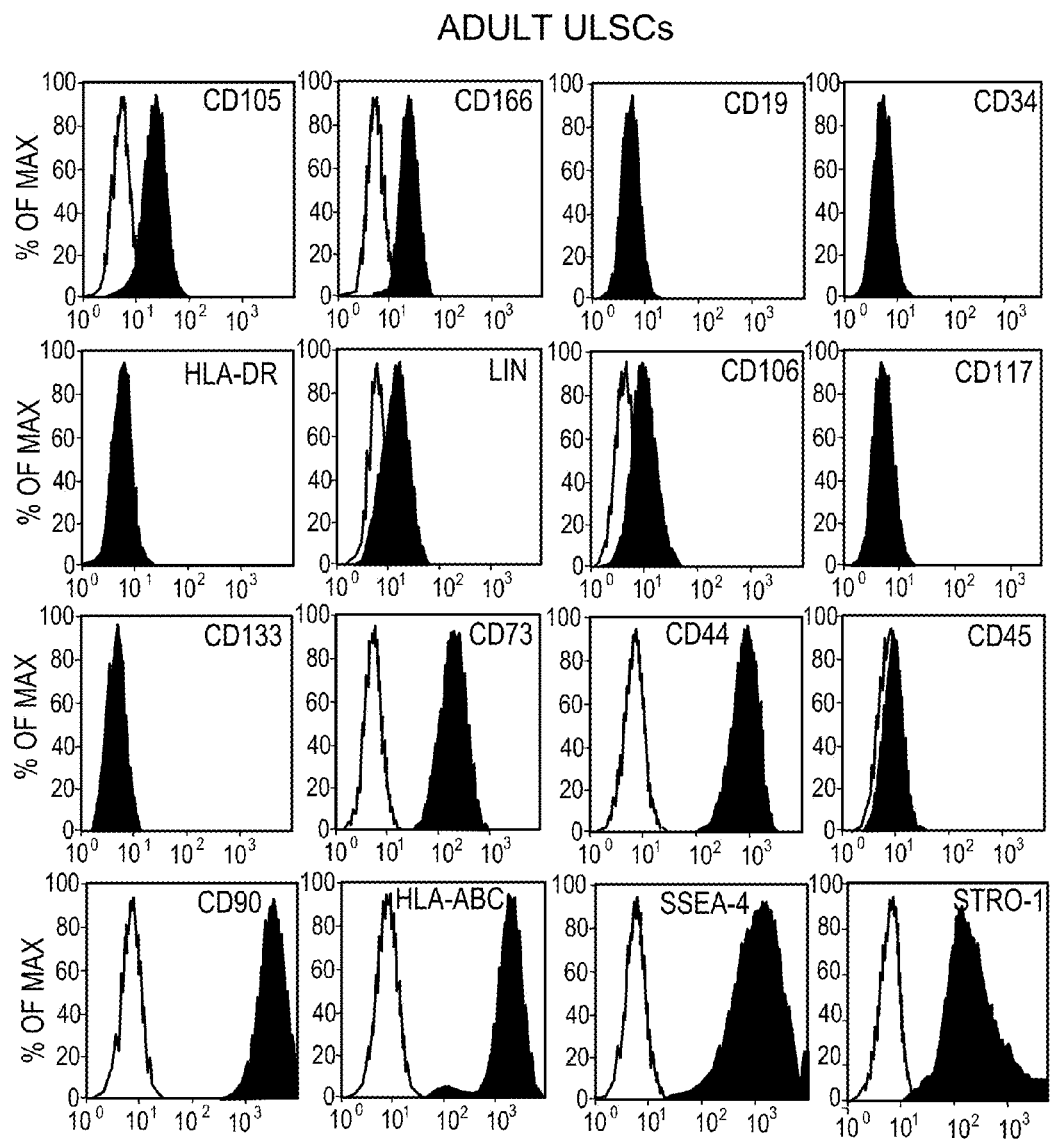

In general, this document provides purified populations of umbilical cord lining stem cells (ULSCs) from human umbilical cord and methods and materials for obtaining such cells. The ULSCs described herein have the capacity to self renew and differentiate into cells from diverse tissue types, including adipogenic cells, osteogenic cells, chondrogenic, neurogenic cells, and cardiogenic cells. The methods and materials described herein allows ULSCs to be isolated and expanded to therapeutically effective numbers in less than 3 weeks, making the methods and cells particularly useful for regenerative medicine. ULSCs also can be modified such that the cells can produce one or more polypeptides or other therapeutic compounds of interest.

Populations and Clonal Lines of ULSCs

Purified populations of ULSCs can be obtained from the lining of a human umbilical cord. As used herein, "purified" means that at least 90% (e.g., 91, 92, 93, 94, 95, 96, 97, 98, or 99%) of the cells within the population are ULSCs. As used herein, "ULSCs" refers to human cells that are positive for CD105, CD106, CD90, CD73, SSEA-4, and STRO-1, negative for CD45, CD34, CD19, and HLA-DR, express OCT-4 and Nanog, and do not express Sox2. "ULSC population" refers to the primary culture obtained from the human umbilical cord sample and uncloned progeny thereof. "Clonal line" refers to a cell line derived from a single cell. As used herein, a "cell line" is a population of cells able to renew themselves for extended periods of times in vitro under appropriate culture conditions. The term "line," however, does not indicate that the cells can be propagated indefinitely.

ULSC populations can be isolated from umbilical cords obtained with informed consent. Typically, after an umbilical cord is obtained in a hospital or clinic, the cord is placed in a hypothermic preservation solution, such as FRS solution from Biolife Solutions (catalog #HTS-FRS) and stored at 4° C. To begin isolating ULSCs, the hypothermic preservation solution can be removed by washing in a buffer, such as Hank's basic salt solution, that is free of $Mg^{2+}$, $Ca^{2+}$, and phenol free. The umbilical cord can be cut into cross sections in the presence of a buffer, and then the cross-sections can be cut longitudinally into two pieces while avoiding any venous or arterial tissue. If any blood is released into the buffer while cutting the cord, the contaminated buffer is replaced with fresh buffer. The longitudinal pieces of cord can be dissected to remove venous and arterial tissue such that the resulting cord lining (i.e., the gelatinous cord material) is substantially free of venous and arterial tissue. As used herein "substantially free of venous and arterial tissue" indicates that as much visible venous and arterial tissue has been removed as possible with manual dissection.

ULSCs can be obtained from the dissected cord lining by culturing the longitudinal pieces of cord lining on a fibronectin coated solid substrate (e.g., a plastic culture device such as a chambered slide or culture flask). The gelatinous surface of the cord lining can be placed in contact with the fibronectin coated solid substrate while the upper surface (i.e., the surface not in contact with the fibronectin coated solid substrate) can be covered with a solid substrate such as a coverslip. Low glucose (i.e., ≤1 g/L glucose) growth medium can be added and the culture device incubated for a time sufficient for cells to migrate from the cord lining to the fibronectin coated solid substrate (e.g., 7 to 10 days). Unless otherwise indicated, cells are cultured at 37° C. in a standard atmosphere that includes 5% $CO_2$. Relative humidity is maintained at about 100%. After ULSCs have adhered to the surface of the fibronectin coated solid substrate, the coverslip can be removed, and the adhered cells can be washed in a buffer such as phosphate-buffered saline (PBS).

A growth medium that can be used for culturing ULSCs is low glucose Dulbecco's Modified Essential Media (DMEM) containing vitamins (choline chloride, D-Calcium pantothenate, Folic Acid, Nicotinamide, Pyridoxal hydrochloride, Riboflavin, Thiamine hydrochloride, and i-Inositol), and non-essential amino acids (glycine, L-alanine, L-Asparagine, L-Aspartic acid, L-Glutamic Acid, L-Proline, and L-Serine). Low glucose DMEM can be supplemented with 10% to 20% serum (e.g., fetal bovine serum (FBS) or human serum), one or more antibiotics (e.g., gentamycin, penicillin, or streptomycin), and glutamine or a stabilized dipeptide of L-alanyl-L-glutamine (e.g., GlutaMax from Invitrogen). In one embodiment, a growth medium can include low glucose DMEM containing vitamins and non-essential amino acids, 15% FBS, 1 to 3% antibiotic (e.g., 2% or 2× gentamycin), and 0.7 to 1.5% (e.g., 1%) of glutamine or a stabilized dipeptide of L-alanyl-L-glutamine. Such a growth medium can be further supplemented with 1 to 100 ng/mL of a growth factor (e.g., basic fibroblast growth factor (bFGF), leukemia inhibitory factor (LIF), or epidermal growth factor (EGF).

In some embodiments, a growth medium further includes insulin, transferrin, selenium, and sodium pyruvate. A particularly useful growth medium can include low glucose DMEM containing vitamins and non-essential amino acids, 15% serum, 1 to 3% antibiotic (e.g., 2% or 2× gentamycin), 0.7 to 1.5% of glutamine or a stabilized dipeptide of L-alanyl-L-glutamine (e.g., 1% or 1× GlutaMax), 1 to 100 ng/mL of a growth factor (e.g., 10 ng/mL bFGF and 10 ng/mL LIF), 0.1 mg/mL to 100 mg/mL of insulin (10 mg/mL), 0.1 mg/mL to 100 mg/mL of transferrin (e.g., 0.55 mg/mL transferring), 0.1 μg/mL to 100 μg/mL selenium (e.g., 0.5 μg/mL selenium), and 0.5 to 1.5% sodium pyruvate (e.g., 1% sodium pyruvate). In some embodiments, such a growth medium further includes 0.05 μg/mL to 100 μg/mL of putrescine (e.g., 10 μg/mL putrescine) and 10 ng/mL of EGF. For embodiments in which an animal free medium is desired, human serum (e.g., 15% human serum) can be used in place of fetal bovine serum.

To subculture ULSC's, TrypZean (Sigma Chemical Co.) can be used to release cells from the solid substrate. The resulting cell suspension can be pelleted and washed with PBS, then seeded into cell culture flasks at approximately 1000 cells/cm$^2$ in a growth medium.

Clonal lines of ULSCs can be established by plating the cells at a high dilution and using cloning rings (e.g., from Sigma) to isolate single colonies originating from a single cell. Cells are obtained from within the cloning ring using trypsin then re-plated in one well of a multi-well plate (e.g., a 6-well plate). After cells reach >60% confluency (e.g., >70% confluency), the cells can be transferred to a larger culture flask for further expansion.

ULSC can be assessed for viability, proliferation potential, and longevity using techniques known in the art. For example, viability can be assessed using trypan blue exclusion assays, fluorescein diacetate uptake assays, or propidium iodide uptake assays. Proliferation can be assessed using thymidine uptake assays or MTT cell proliferation assays. Longevity can be assessed by determining the maximum number of population doublings of an extended culture.

ULSCs can be immunophenotypically characterized using known techniques. For example, the cells can be fixed (e.g., in paraformaldehyde), permeabilized, and reactive sites blocked (e.g., with serum albumin), then incubated with an antibody having binding affinity for a cell surface antigen such as CD19, CD34, CD45, CD73, CD90, CD105, CD106, SSEA-4, STRO-1, and HLA-DR, or any other cell surface antigen. The antibody can be detectably labeled (e.g., fluorescently or enzymatically) or can be detected using a secondary antibody that is detectably labeled. In some embodiments, the cell surface antigens on ULSCs can be characterized using flow cytometry and fluorescently labeled antibodies.

ULSCs also can be characterized based on the expression of one or more genes. Methods for detecting gene expression can include, for example, measuring levels of the mRNA or protein of interest (e.g., by Northern blotting, reverse-transcriptase (RT)-PCR, microarray analysis, Western blotting, ELISA, or immunohistochemical staining)

As described herein, ULSCs generally are positive for the cell surface markers CD105, CD106, CD90, CD73, SSEA-4, and STRO-1, and negative for CD45, CD34, CD19, and HLA-DR, express OCT-4 and Nanog, and do not express Sox2. As used herein, the phrase "do not express" indicates that mRNA was not detected as compared with suitable positive and negative controls processed and analyzed under similar conditions. This suite of cell surface markers, including CD19, CD34, CD45, CD73, CD90, CD105, CD106, STRO-1, SSEA-4, and HLA-DR, and expression profile for Oct4, Nanog, and Sox2 can be used to identify ULSCs, and to distinguish ULSCs from other stem cell types.

ULSCs can be cryopreserved by suspending the cells (e.g., up to 5×10$^6$ cells/mL) in a cryopreservative such as dimethylsulfoxide (DMSO, typically 10%). In some embodiments, a freezing medium such as CryoStor from Biolife solutions is used to cryopreserve the cells. After adding cryopreservative, the cells can be frozen (e.g., to −90° C.). In some embodiments, the cells are frozen at a controlled rate (e.g., controlled electronically or by suspending the cells in a bath of 70% ethanol and placed in the vapor phase of a liquid nitrogen storage tank. When the cells are chilled to −90° C., they can be placed in the liquid phase of the liquid nitrogen storage tank for long term storage. Cryopreservation can allow for long-term storage of these cells for therapeutic use.

Differentiation of ULSCs

ULSCs are capable of differentiating into a variety of cells of the mesoderm lineage, including adipogenic cells, osteogenic cells, chondrogenic cells, and cardiogenic cells as well as cells of the ectoderm lineage (e.g., neurogenic cells). As used herein, "capable of differentiating" means that a given cell, or its progeny, can proceed to a differentiated phenotype under the appropriate culture conditions. Differentiation can be induced using one or more differentiation agents, including any chemical, cytokine, protein, peptide, or any other substance that is capable of inducing differentiation of a cell. Non-limiting examples of differentiation agents include without limitation, $Ca^{2+}$, an epidermal growth factor (EGF), a platelet derived growth factor (PDGF), a keratinocyte growth factor (KGF), a transforming growth factor (TGF), cytokines such as an interleukin, an interferon, or tumor necrosis factor, retinoic acid, transferrin, hormones (e.g., androgen, estrogen, insulin, prolactin, triiodothyronine, hydrocortisone, or dexamethasone), sodium butyrate, TPA, DMSO, NMF (N-methyl formamide), DMF (dimethylformamide), or matrix elements such as collagen, laminin, or heparan sulfate.

Determination that ULSCs have differentiated into a particular cell type can be assessed using known methods, including measuring changes in morphology and cell surface markers (e.g., by flow cytometry or immunohistochemistry), examining morphology by light or confocal microscopy, or by measuring changes in gene expression using techniques such as PCR or gene-expression profiling.

For example, ULSCs can be induced to differentiate into osteogenic cells using an induction medium (e.g., AdvanceSTEM™ Osteogenic Differentiation medium, catalog #SH30881.02 from HyClone or Osteogenic Differentiation medium from Lonza, catalog #PT-3002). Typically, osteogenic induction media contain dexamethasone, L-glutamine, ascorbate, and β-glycerophosphate (Jaiswal et al., *J. Biol. Chem.* 64(2):295-312 (1997)), and in some embodiments, antibiotics such as penicillin and streptomycin. Osteogenic differentiation can be detected by testing for the presence of osteogenic markers, which include, but are not limited to, osteopontin (OP), osteocalcin (OC), osteonectin (ON), bone sialoprotein, and Distal-less homeobox 5 (DLX5). Osteogenesis also can be detected by using von Kossa stain (Jaiswal et al., supra) and/or alizarin red stain (Wan et al., *Chin. J. Traumatol.* 5:374-379 (2002)), which detect the presence of calcium deposits.

ULSCs can be induced to differentiate into adipogenic cells using an induction medium (e.g., AdvanceSTEM™ Adipogenic Differentiation Medium from HyClone, catalog #SH30886.02; or Adipogenic Differentiation Medium, catalog #PT-3004, from Lonza). Typically, adipogenic differentiation media contain human insulin, L-glutamine, dexamethasone, indomethacin, and 3-isobutyl-1-methyl-xanthine. For example, ULSCs can be cultured in Adipogenesis Differentiation Medium for 3 days (at 37° C., 5% $CO_2$), followed by 1 day of culture in Adipogenesis Maintenance Medium (catalog #PT-3102A, from Lonza) containing human insulin and L-glutamine. After 3 complete cycles of induction/maintenance, the cells can be cultured for an additional 7 days in Adipogenesis Maintenance Medium, replacing the medium every 2-3 days.

Adipogenic cells contain lipid filled liposomes that can be visualized with Oil Red stain (Conget and Minguell, *J. Cellular Physiology* 181:67-73, (1999)). Such cells also contain trigycerides, which fluoresce green with Nile Red stain (Fowler and Greenspan, *Histochem. Cytochem.* 33:833-836 (1985)). Adipogenic differentiation also can be assessed by testing for the presence of adipogenic transcription factors PPARy2 (peroxisome proliferator activated receptor gamma) and/or CEBPα (CCAAT/enhancer binding protein alpha), or for lipoprotein lipase by methods such as immunohistochemistry and RT-PCR.

ULSCs can be induced to differentiate into chondrogenic cells using an induction medium (e.g., AdvanceSTEM™ Chondrogenic Differentiation Medium from HyClone, catalog #SH30889.02, or Chondrogenic Differentiation Medium from Lonza, catalog #PT-3003). Typically, chondrogenic differentiation media contain dexamethasone, ascorbate, sodium pyruvate, proline, L-glutamine, and TGF-β3. Chondrogenic cells contain sulfate proteoglycans that can be visualized with Alcian Blue stain. Such cells also contain Type II collagen. Chondrogenic differentiation also can be assessed by testing for the presence of aggrecan and/or link protein.

ULSCs can be induced to differentiate into neurogenic cells using an induction medium. Typically, neurogenic differentiation media contain growth factors such as basic fibroblast growth factor (bFGF) and EGF; or sonic hedgehog (SHH), FGF, and bFGF; EGF or brain derived neurotrophic factor (BDNF), and glial derived neurotrophic factor (GDNF)). Retinoic acid (RA) and ascorbic acid also can be included in a neurogenic differentiation medium. For example, ULSCs can be cultured on fibronectin or Matrigel™ coated plates in the presence of media containing putrescine and growth factors (bFGF and EGF, or SHH, FGF8, and bFGF) for 12 days, wherein RA is added to the cultures from days 10-12. After incubating in such media for 12 days, the media can be replaced with media containing EGF or BDNF, GDNF, and ascorbic acid, and the cells incubated for an additional 14 days. Neurogenic differentiation can be assessed by testing for the presence of nestin, class III beta-tubulin (tubulin β-4), glial fibrillary acidic protein (GFAP), neuro-specific enolase (NSE), microtubule-associated protein 2 (MAP2), or galactocerebroside (GalC).

ULSCs can be induced to differentiate into cardiogenic cells using an induction medium. Typically, cardiogenic differentiation media contain 5-AZA-2'-deoxycytidine (Aza). Cardiogenic differentiation can be assessed by testing for the presence of cardiac markers such as demin, troponin I, troponin T, or atrial natriuretic factor (ANF).

In some embodiments, the ULSCs can be cultured or seeded onto bio-compatible scaffolds. Such scaffolds can act as a framework that supports the growth of the cells in multiple layers. Scaffolds can be molded into the desired shape for facilitating the development of tissue types. For example, the cells can be seeded on a scaffold and induced to differentiate into osteogenic cells or chondrogenic cells as discussed above.

Typically, the scaffold is formed from collagen or a polymeric material. Biodegradable scaffolds are particularly useful such that after implantation into an animal, the scaffold can be absorbed into the animal matter over time. Suitable polymeric scaffolds can be formed from monomers such as glycolic acid, lactic acid, propyl fumarate, caprolactone, hyaluronan, hyaluronic acid, and combinations thereof. Other scaffolds can include proteins, polysaccharides, polyhydroxy acids, polyorthoesters, polyanhydrides, polyphosphazenes, synthetic polymers (particularly biodegradable polymers), and combinations thereof. The scaffold also can include hormones, growth factors, cytokines, and morphogens (e.g., retinoic acid), desired extracellular matrix molecules (e.g., fibronectin), or other materials (e.g., DNA, viruses, other cell types, etc.). See, e.g., U.S. Pat. No. 7,470, 537.

The ULSCs can be loaded into the scaffold by soaking the scaffold in a solution or suspension containing the ULSCs, or the ULSCs can be infused or injected into the scaffold. In other embodiments, a hydrogel can be formed by crosslinking a suspension including the desired polymer and the ULSCs, allowing the ULSCs to be dispersed throughout the scaffold. To direct the growth and differentiation of the desired structure, the scaffold containing the ULSCs can be cultured ex vivo in a bioreactor or incubator, as appropriate. In other embodiments, the scaffold containing the ULSCs can be implanted within a host animal directly at the site in which it is desired to grow the tissue or structure. In still another embodiment, the scaffold containing the ULSCs can be engrafted on a host (typically an animal such as a pig), where it can grow and mature until ready for use.

Modified Populations of ULSCs

ULSCs can be modified such that the cells can produce one or more polypeptides or other therapeutic compounds of interest. To modify the isolated cells such that a polypeptide or other therapeutic compound of interest is produced, the appropriate exogenous nucleic acid must be delivered to the cells. In some embodiments, the cells are transiently transfected, which indicates that the exogenous nucleic acid is episomal (i.e., not integrated into the chromosomal DNA). In other embodiments, the cells are stably transfected, i.e., the exogenous nucleic acid is integrated into the host cell's chromosomal DNA. The term "exogenous" as used herein with reference to a nucleic acid and a particular cell refers to any nucleic acid that does not originate from that particular cell as found in nature. In addition, the term "exogenous" includes a naturally occurring nucleic acid. For example, a nucleic acid encoding a polypeptide that is isolated from a human cell is an exogenous nucleic acid with respect to a second human cell once that nucleic acid is introduced into the second human cell. The exogenous nucleic acid that is delivered typically is part of a vector in which a regulatory element such as a promoter is operably linked to the nucleic acid of interest.

Cells can be engineered using a viral vector such as an adenovirus, adeno-associated virus (AAV), retrovirus, lentivirus, vaccinia virus, measles viruses, herpes viruses, or bovine papilloma virus vector. See, Kay et al. *Proc. Natl. Acad. Sci. USA* 94:12744-12746 (1997) for a review of viral and non-viral vectors. A vector also can be introduced using mechanical means such as liposomal or chemical mediated uptake of the DNA. For example, a vector can be introduced into ULSCs by methods known in the art, including, for example, transfection, transformation, transduction, electroporation, infection, microinjection, cell fusion, DEAE dextran, calcium phosphate precipitation, liposomes, LIPO-FECTIN™, lysosome fusion, synthetic cationic lipids, use of a gene gun or a DNA vector transporter.

A vector can include a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyl-transferase (XGPRT). Such markers are useful for selecting stable transformants in culture.

ULSCs also can have a targeted gene modification. Homologous recombination methods for introducing targeted gene modifications are known in the art. To create a homologous recombinant ULSCs, a homologous recombination vector can be prepared in which a gene of interest is flanked at its 5' and 3' ends by gene sequences that are endogenous to the genome of the targeted cell, to allow for homologous recombination to occur between the gene of interest carried by the vector and the endogenous gene in the genome of the targeted cell. The additional flanking nucleic acid sequences are of sufficient length for successful homologous recombination with the endogenous gene in the genome of the targeted cell. Typically, several kilobases of flanking DNA (both at the 5' and 3' ends) are included in the vector. Methods for constructing homologous recombination vectors and homologous recombinant animals from recombinant stem cells are commonly known in the art (see, e.g., Thomas and Capecchi, *Cell* 51:503 (1987); Bradley, *Curr. Opin. Bio/Technol.* 2:823-29 (1991); and PCT Publication Nos. WO 90/11354, WO 91/01140, and WO 93/04169.

Compositions and Articles of Manufacture

This document also features compositions and articles of manufacture containing purified populations of ULSCs or clonal lines of ULSCs. In some embodiments, the purified population of ULSCs or clonal line is housed within a container (e.g., a vial or bag). In other embodiments, a culture medium (e.g., animal free growth medium) is included in the composition or article of manufacture. In still other embodiments, the composition or article of manufacture can include one or more cryopreservatives. In some embodiments, ULSCs or clonal lines can be formulated as pharmaceutical compositions.

Generally, a pharmaceutical composition includes a pharmaceutically acceptable carrier, additive, or excipient and is formulated for an intended mode of delivery, e.g., intravenous, subcutaneous, or intramuscular administration, or any other route of administration described herein. For example, a pharmaceutical composition for intravenous administration can include a physiological solution, such as physiological saline and water, Ringers Lactate, dextrose in water, Hanks Balanced Salt Solution (HBSS), Isolyte S, phosphate buffered saline (PBS), or serum free cell media (e.g., RPMI). Pharmaceutical compositions also can include, e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH of a composition can be adjusted with acids or bases, such as hydrochloric acid or sodium hydroxide.

Pharmaceutical compositions should be stable under the conditions of processing and storage and must be preserved against potential contamination by microorganisms such as bacteria and fungi. Prevention of contamination by microorganisms can be achieved by various antibacterial and antifungal agents, e.g., antibiotics such as aminoglycosides (e.g., kanamycin, neomycin, streptomycin, and gentamicin), ansaycins, and quinalones.

The pharmaceutical composition can be formulated to include one or more additional therapeutic agents. For example, a composition can be formulated to include one or more growth factors and/or one or more anti-inflammatory agents, including non-steroidal anti-inflammatory drugs, dexamethasone or other types glucocorticoid steroids, PDGF, EGF, fibroblast growth factor-2, stem cell factor, a bone morphogenic protein (BMP) such as BMP-2 or BMP-7, methylsulfonylmethane (MSM), glucosamine, or chondroitin sulfate.

Purified populations of ULSCs or clonal ULSC lines can be combined with packaging material and sold as a kit. The packaging material included in a kit typically contains instructions or a label describing how the purified populations of ULSCs or clonal lines can be grown, differentiated, or used. Components and methods for producing such kits are well known.

An article of manufacture or kit also can include one or more reagents for characterizing a population of ULSCs or a clonal ULSC line. For example, a reagent can be a nucleic acid probe or primer for detecting expression of a gene such as Oct4, Nanog, or Sox2. Such a nucleic acid probe or primer can be labeled, (e.g., fluorescently or with a radioisotope) to facilitate detection. A reagent also can be an antibody having specific binding affinity for a cell surface marker such as CD19, CD34, CD45, CD73, CD90, CD105, CD106, STRO-1, SSEA-4, or HLA-DR. An antibody can be detectably labeled (e.g., fluorescently or enzymatically). Other components, such as a scaffold (e.g., a scaffold composed of collagen), also can be included in a composition or article of manufacture. The scaffold can be seeded with ULSCs as described above.

Methods of Using ULSCs

Populations of ULSCs or clonal lines of ULSCs can be used to treat subjects having a variety of disorders or injuries. The ULSCs or clonal lines can be delivered to a subject in various ways as appropriate to deliver stem cells, including, but not limited to oral or parenteral routes of administration such as intravenous, intramuscular, intraperitoneal, subcutaneous, intrathecal, intraarterial, or nasal. In some embodiments, two or more routes of administration can be used to deliver the stem cells. In other embodiments, the cells are delivered to a site of the injury.

Effective amounts of ULSCs or clonal lines can be determined by a physician, taking into account various factors such as overall health status, body weight, sex, diet, time and route of administration, other medications, and any other relevant clinical factors. In some embodiments, between 500,000 and 2,000,000 (e.g., 500,000 to 1,000,000; 500,000 to 750,000; 750,000 to 1,000,000; 750,000 to 2,000,000; 750,000 to 1,500,000; 1,000,000 to 2,000,000; 1,000,000 to 1,500,000; or 1,500,000 to 2,000,000) stem cells/kg weight of the subject can be delivered to the subject in total. In some embodiments, about $1.2 \times 10^6$ ULSCs/kg weight of the subject are delivered to the subject.

In some embodiments, between 500,000 and 500,000,000 (e.g., $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, or $5 \times 10^8$) ULSCs/kg weight of the subject can be delivered to the subject in total.

In some embodiments, ULSCs are delivered to the subject only once. In some embodiments, multiple (e.g., two, three, four, five, six, seven, eight, nine, 10, 11, 12, 13, 14, 15, or 20 or more) deliveries are made. For example, multiple deliveries of ULSCs can be made over the course of several (e.g., two, three, four, five, six, seven, eight, nine, 10, 14, 21, 28, or 31 or more) consecutive days (e.g., one delivery each day for seven days or one delivery every other day for seven days). ULSCs can be delivered to a subject for several months (e.g., one delivery per month for six months, or one delivery per week for two months).

ULSCs can be delivered to a subject at various time points after an injury or disease diagnosis. For example, the cells can be delivered immediately following an injury (e.g., from 1 to 8 such as 1.5, 2, 2.5, 3, 3.5, 4, 4.5, 5, 5.5, 6, 6.5, 7, 7.5, or 8 hours after the injury occurs). The cells can be delivered to a subject less than 10 (e.g., 9, 8, 7, 6, 5, 4, 3, 2, or 1) days after an injury occurs. The cells can be delivered to a subject less than 6 (e.g., 5, 4, 3, 2, or 1) weeks after an injury occurs. In some embodiments, ULSCs can be delivered to a subject up to 10 years (e.g., 9, 8, 7, 6, 5, 4, 3, 2, or 1) years after an injury occurs. The compositions and methods described herein can be used at any time following an injury or during the course of a chronic injury.

It is understood that regardless of the site, combination of sites, route of administration, combination of routes, a therapeutically effective amount of ULSCs (or a composition that includes the ULSCs) is delivered to the subject. As used herein, an "effective amount" or "therapeutically effective amount" of a composition or ULSCs is the amount that is sufficient to provide a beneficial effect to the subject to which the composition or cells are delivered. The effective amount can be the amount effective to achieve an improved survival rate, a more rapid recovery, an improvement in the quality of life, or an improvement or elimination of one or more symptoms associated with a subject's condition.

The efficacy of a given treatment in treating a particular disorder or an injury can be defined as an improvement of one or more symptoms of the disorder or injury by at least 5% (e.g., at least 10%, at least 15%, at least 20%, at least 25%, at least 30%, at least 40%, at least 50%, at least 55%, at least 60%, at least 65% or more). In some cases, efficacy of a treatment with ULSCs can be determined from the stabilization of one or more worsening symptoms associated with the injury (i.e., the treatments curtail the worsening of one or more symptoms of the injury). ULSCs or pharmaceutical compositions containing ULSCs can be administered to a subject in combination with another treatment, e.g., a treatment for a bone injury. For example, the subject can be administered one or more additional agents that provide a therapeutic benefit to the subject who has a bone injury. Additional therapeutic agents include, e.g., growth factors and/or anti-inflammatory agents (e.g., non-steroidal anti-inflammatory drugs, dexamethasone or other types glucocorticoid steroids, PDGF, EGF, fibroblast growth factor-2, stem cell factor, a bone morphogenic protein (BMP) such as BMP-2 or BMP-7, methylsulfonylmethane (MSM), glucosamine, or chondroitin sulfate. The ULSCs or pharmaceutical compositions and the one or more additional agents can be administered at the same time or sequentially.

The invention is further described in the following examples, which do not limit the scope of the invention described in the claims.

EXAMPLES

Example 1

Compositions for Culturing and Expanding ULSCs

The following compositions were prepared for use in culturing and expanding ULSCs:
Composition 1 (ULSC Growth Medium):
DMEM, low glucose and phenol free (catalog #11054-020, Invitrogen)
15% Fetal Bovine Serum (FBS) that is characterized or premium select (catalog #SH30611.02, HyClone)
1× or 1% GlutaMAX (catalog #35050-061, Invitrogen)
2× or 2% Gentamicin (gentamicin sulfate 60, 80, or 100 mg, catalog #0409-3400-01, 0409-3401-01, or 0409-3402-01, respectively, from Hospira; or gentamicin cell culture 50 mg, catalog #15750-060, Invitrogen)
1× or 1% MEM Vitamin Solution (catalog #11120-052, Invitrogen)
1× or 1% MEM NEAA (non essential amino acids) (catalog #11140-050, Invitrogen).
Composition 2:
DMEM low glucose (phenol free)
15% Fetal Bovine Serum (FBS) that is characterized or premium select
1× or 1% GlutaMAX
2× or 2% Gentamicin
1× or 1% MEM Vitamin Solution
1× or 1% MEM NEAA
10 ng/mL basic fibroblast growth factor (bFGF) (catalog #1008, CellGenix, recombinant human bFGF)
10 ng/mL Leukemia inhibitory factor (LIF) (catalog #L5283, Sigma, recombinant human LIF).
Composition 3:
DMEM low glucose (phenol free)
15% Human Serum A/B (HS-A/B) (HS-A/B, obtained from Sigma, catalog #H4522; Atlanta Biologicals, catalog #S40110; or Gemini BioProducts, catalog #100-512)
1× or 1% GlutaMAX
2× or 2% Gentamicin
1× or 1% MEM Vitamin Solution
1× or 1% MEM NEAA
1.0 mg/mL insulin (human insulin, recombinant from S. cerevisiae, catalog #I9278, Sigma; human insulin, recombinant from E. coli, catalog #Huminilin N, Eli Lily and Co.; or catalog #12585-014, Invitrogen, 4 mg/mL solution of recombinant human insulin)
0.55 mg/mL transferrin (human holo-transferrin, Mebiopharm Co., Ltd.)
0.5 µg/mL selenium (sodium selenite, catalog #S9133, Sigma)
1× or 1% sodium pyruvate (hybrid-Max, catalog #P3662-100G, Sigma; or 100 mM solution, catalog #S8636-100ML, Sigma)
10 ng/mL bFGF
10 ng/mL LIF.
Composition 4:
DMEM low glucose (phenol free)
15% Human Serum A/B
1× or 1% GlutaMAX
2× or 2% Gentamicin
1× or 1% MEM Vitamin Solution
1× or 1% MEM NEAA
1.0 mg/mL insulin
0.55 µg/mL transferrin
0.5 µg/mL selenium
1× or 1% sodium pyruvate
10 µg/mL putrescine (catalog #P6024, Sigma)
10 ng/mL bFGF
10 ng/mL LIF
10 ng/mL epidermal growth factor (EGF) (catalog #E9644, Sigma, recombinant human EGF).

Example 2

Obtaining, Culturing, and Expanding ULSCs

Umbilical cords (UCs) were obtained through an IRB approved protocol with appropriate informed consent from a clinic or hospital. In preparation for culturing explants of UCs, 1 ml of human fibronectin (1 µg/ml, catalog #F0895, Sigma) is added to each well of a 6 well dish (catalog #140675, Nunc). The coated dish is kept for at least 30 minutes at room temperature or until the explants are ready for culturing. Other cell culture flasks were used in experiments described below, including T25, T75, and T225 flasks (catalog #353109, 353136, and 353139, respectively, BD Falcon); HYPERFlask 1700 $cm^2$ (catalog #10024, Corning); cell stack, single or multiple (catalog #3268, Corning); and 10 cm cell culture dish (catalog #150350, Nunc). In some experiments, cell culture bags (catalog PL325, OriGen Biomedical) were used.

Approximately 7 cm of UC is obtained, placed into a 50 mL tube with sterile FRS solution (catalog #HTS-FRS, Biolife Solutions) at 4° C. and transported to the laboratory. Upon arrival in the laboratory, the FRS solution is removed and the UC is washed with 3× Hank's basic salt solution (HBBS) that is $Mg^{2+}$, $Ca^{2+}$, and phenol free (catalog

SH30588, HyClone). The UC then is placed in a 10% betadine solution with HBSS for 1 minute, followed by three washes in HBSS or until all betadine is removed. The UC is placed into a 10 cm dish with HBSS. The tissue is cut into 0.5-1 cm cross sections using a scapel with a number 10 or 11 blade (catalog #371619, BD). The cross sections are placed into a new 10 cm dish with fresh HBSS and cut longitudinally, while avoiding the vein and both arteries. If any blood is released into the dish while cutting the tissue, the contaminated HBSS is replaced with fresh HBSS. The two longitudinal pieces are placed into a new 10 cm dish with fresh HBSS, making sure to know the location of the gelatinous material (cord lining). With fine forceps, the vein and both arteries are dissected out and discarded. Care is taken to remove as much venous and arterial tissue as this tissue will contaminate the culture with endothelial cells.

The dissected cord lining is placed in fresh HBSS. Sterile coverslips (22 mm×22 mm, catalog #12-565-28, Nunc), forceps (catalog #12576-934, VWR), and 6 well plates are obtained for seeding of the explants. One longitudinal piece of tissue is cut into 3-4 strips with the gelatinous side up. Each strip is lifted with a fine forcep and placed into a well of a fibronectin coated six well plate, gelatinous side down, where the human fibronectin is aspirated before placing the explants into the well. Three to four strips are placed in a single well. Sterile coverslips are placed carefully on top of the cord lining and 2 mL of growth medium is placed into the well. The six well plate is incubated at 5% $CO_2$ and 37° C. immediately after all explants are in place.

To establish ULSC's, a half medium change is performed every over day while being careful to not disturb the coverslip or explants. At day 7 following the start of culturing (and no longer than 10 days), the area around the explants is visualized for cell migration. If there is a substantial amount of cells migrating off of the explants, the coverslip and explants are removed, taking care to not disturb the adhered cells. After removing the coverslips and explants, cells are washed in PBS ($Mg^{2+}$, $Ca^{2+}$, phenol free, catalog #SH30256, HyClone) and fed with 2 mL of fresh medium at 37° C. Cells are cultured until the plate is approximately 60% confluent.

To subculture ULSC's, the reagents, including the medium, PBS, human serum type A/B (HS-A/B, obtained from Sigma, catalog #H4522; Atlanta Biologicals, catalog #S40110; or Gemini BioProducts, catalog #100-512), and TrypZean (catalog #T349-500 mL, Sigma) are prewarmed before using. In addition, the cell culture flasks are prepared by adding human fibronectin to the flask a minimum of 0.5 hours before use. Medium from the cells to be subcultured is aspirated, and the cells washed with PBS. After removing the PBS, TrypZean is added to each well and the flask incubated in a 5% $CO_2$ incubator at 37° C. for approximately 5 minutes. Cells then are checked under a microscope to assure that the cells are lifted. The cell suspension is removed and placed into a 50 mL tube. PBS is added to the flask to wash remainder of the cells then placed into the same 50 mL tube containing the cell suspension. To stop the reaction of TrypZean, FBS (catalog #SH30611.02, HyClone) or HS-A/B is added to 10% of the solution and swirled to mix. The cell suspension is spun at 400×g for 5 minutes at 4° C. to pellet the cells, which then are resuspended in 5 mL of medium. Human fibronectin is removed from the culture flask and then cells are seeded at 1000 cells/$cm^2$ in media 1, 2, 3, or 4. The remainder of the cells (~10×$10^6$ cells) can be frozen at 2.5×$10^6$ cells/mL in four separate vials.

ULSCs are frozen using no more than 5×$10^6$ cells/mL of freezing medium (CryoStor CS-10, catalog CS-10, Biolife Solutions). The cell suspension is spun at 400×g for 5 minutes at 4° C. then CS-10 freezing medium is added dropwise. After adding the appropriate amount of CS-10, cells are aliquoted into cryovials, which are placed in a rate control freezer to begin cryopreservation. For long term storage, cells are transferred to a liquid nitrogen ($LN_2$) dewar.

When ULSCs are thawed, the medium is pre-warmed and human fibronectin is coated on cell culture flasks for at least 0.5 hours before culture. Cryovials are quickly removed from $LN_2$, placed in a 37° C. water bath, and vigorously shaken. Cell suspension is removed from cryovial and placed in a 15 mL tube. Pre-warmed medium is added drop wise at a rate of 1 mL per minute for washing the cells. The cell suspension is spun at 400×g for 5 minutes at 4° C. and the medium aspirated. The cell pellet is resuspended in medium and the cells counted. Cells are seeded at 1000 cells/$cm^2$ into cell culture flasks after removing human fibronectin from the flask.

Example 3

Characterization of ULSCs

Figure 2:
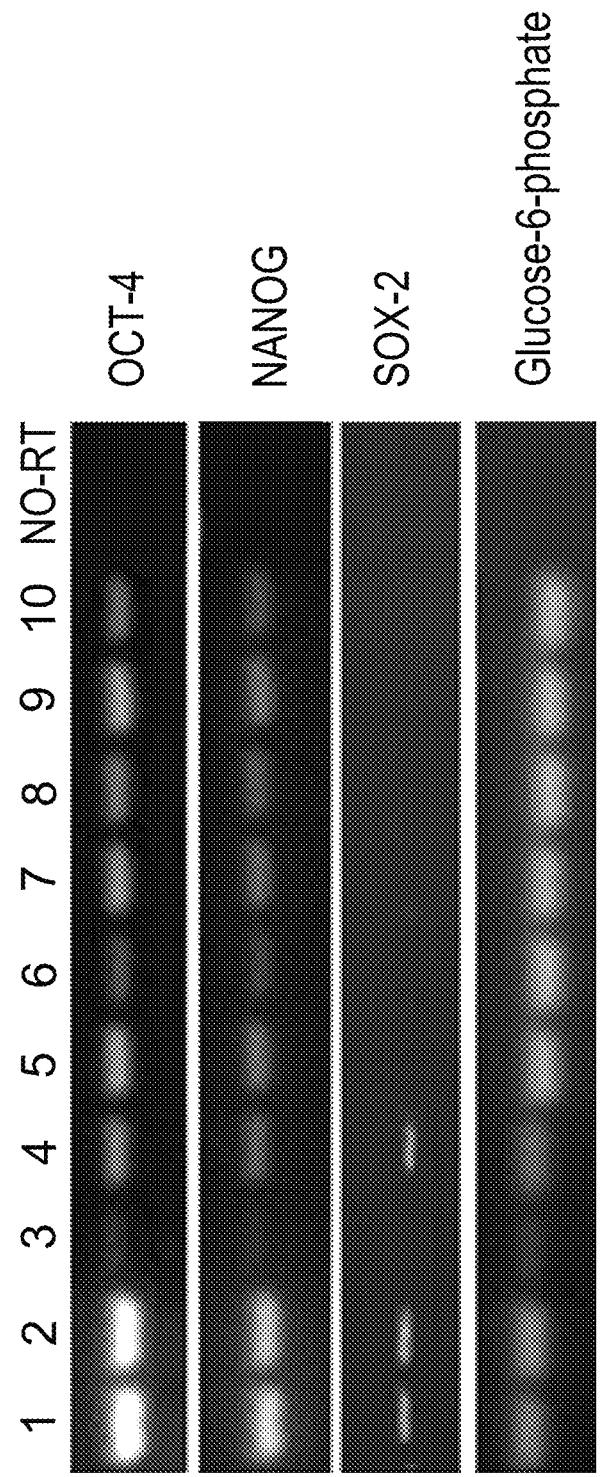
FIG. 2 contains a representative image of a gel from the RT-PCR analysis of OCT-4, Nanog, SOX-2, and glucose-6-phosphate in NT2 control cells (lane 1), gonadal tissue (lane 2), prenatal umbilical cord tissue (lane 3), adult umbilical cord tissue (lane 4), prenatal ULSCs passage 3 (lane 5); prenatal ULSCs passage 2 (lane 6), prenatal ULSCs passage 1 (lane 7), adult ULSCs passage 1 (lane 8), adult ULSCs passage 2 (lane 9), and adult ULSCs passage 3 (lane 10).

Umbilical cords were obtained and grown as explants onto 6 well coated dishes as described in Example 2. All plates were treated with human fibronectin (1 µg/ml) unless otherwise stated. Briefly, once the 6 well dishes became 60-70% confluent, umbilical cord lining stem cells (ULSCs) were enzymatically detached and passaged onto T225 flask at a density of 1000 cells per $cm^2$ using ULSC Growth media (DMEM low glucose (phenol free), 15% FBS that is characterized or premium select, Glutamax (1× or 1%), Gentamycin (2× or 2%), MEM Vitamin Solution (1× or 1%), and MEM NEAA (1× or 1%)). At passage 3, approximately 8.0×$10^6$ cells were obtained for FACS and stained in 8 different tubes for analysis using 16 different markers (CD105, CD166, CD19, CD34, HLA-DR, LIN, CD106, CD117, CD133, CD73, CD44, CD45, CD90, HLA-ABC, SSEA-4, and STRO-1). As shown in FIG. 1, ULSCs were positive for CD105, CD166, LIN, CD106, CD73, Cd44, CD90, HLA-ABC, SSEA-4, and STRO-1, and negative for CD19, CD34, CD45, CD117, and CD133. In adult ULSCs there is an upregulation of the marker STRO-1 which is a defined mesenchymal stem cells marker. There is also a negligible increase in the leukocytes marker CD45. Expression of OCT-4, Nanog, SOX-2, and glucose-6-phosphate was assessed by RT-PCT in NT2 control cells, gonadal cells, prenatal umbilical cord tissue (i.e., umbilical cord tissue obtained from spontaneous abortions), and adult umbilical cord tissue (i.e., umbilical cord tissue obtained after delivery of full-term baby). Cells from prenatal or adult umbilical cord blood expressed OCT-4 and Nanog but not Sox2. See FIG. 2. FACS analysis of both types of cord demonstrates slight changes in marker expression.

At passage 3, cells were detached and plated onto 12 well dishes at a density of 50,000 cells per well for cardiac differentiation, neural differentiation, adipose differentiation, osteogenic differentiation, chondrocyte differentiation, and colony forming unit assay. At each passage and for each differentiation, an aliquot of cells was taken for RNA analysis of different conditions. Appropriate controls were included in each differentiation condition. The media used is ULSCs growth media described above.

Cardiac Differentiation—Cells were plated using ULSCs growth medium and the following day 10 µM 5-azacytidine was added for 24 hour incubation. The following day fresh ULSCs growth medium was added. At 1 week, cells were treated again with 10 µM 5-azacytidine for 24 hours as described above. At 21 days following the first treatment of 5-azacytidine, some wells were collected for RNA analysis and the remainder were used for ICC. Cardiac differentiation was confirmed by staining for myosin heavy chain, troponin I, sarcomeric actin, desmin, and connexin 43.

Neural Differentiation—cells were plated using a 50/50 blend of ULSCs growth medium and a neural differentiation media composed of KO DMEM (KnockOut™ DMEM, catalog #10829-018, Invitrogen), 10% serum replacement, 1× MEM vitamins, NEAA, Pen Strep, glutaMAX, N2, and ITS premix. All cells were plated onto matrigel coated plates. Growth factors added to the neural media were bFGF and EGF at 20 ng/ml or SHH (sonic hedgehog) (100 ng/ml), FGF8 (100 ng/ml) and bFGF (20 ng/ml). After 24 hours, cells were washed and fed with 100% neural media. At 7 days added 3 uM retinoic acid (RA) for 3 consecutive days directly to the media. On the $3^{rd}$ day, 50% of the media was changed to DMEM:F12 (catalog #10565, Gibco) with the same supplements as KO DMEM described above. The following day, 100% DMEM:F12 neural growth medium was used and the growth factors were changed for terminal differentiation as follows. Cells on SHH, FGF8, and bFGF were switched to GDNF (20 ng/ml), BDNF (20 ng/ml), and Ascorbic Acid (200 µM). For cells on bFGF+EGF, just the bFGF was removed for terminal differentiation. Cells were left for terminal differentiation for an additional 10-14 days, while being fed every 3-4 days. Some wells were taken for RNA analysis and the remainders were fixed for ICC. Differentiation to neural cells was confirmed by nestin, A2B5, O4, and β-tubulin III staining Adipose Differentiation—after seeding cells they were left to become 90% confluent at which time they were switched to Lonza's Adipogenic differentiation media according to manufacturer's protocol. 3 days induced and 2 days maintained for 21 days total. Differentiation to adipose was confirmed by Oil Red O staining of fat vacuoles.

Osteogenic Differentiation—after seeding, cells were left to become 90% confluent at which time they were switched to Hyclone Osteogenic differentiation media according to manufacturer's protocol for 21 days. Differentiation to osteogenic cells was confirmed using alizarin red S, which stains calcium deposits.

Chondro Differentiation—cells were pelleted at 500,000 cells per 15 ml conical tube and fed with Hyclone chondrogenic differentiation media according to manufacturer's protocol for 28 days. Chondrocyte differentiation was confirmed using 1% alcian blue, which stains sulfated proteoglycans.

Colony Forming Unit Assay: an aliquot of 20,000 cells were obtained and 20 mL of ULSC growth medium was used to resuspend the cells. A 10 mL aliquot was added to a precoated 10 cm dish and labeled as control, 10,000 cells. An aliquot of 500 µL (500 cells) was placed into 49.5 mL of medium. Cells were resuspended and seeded (10 mL) into 5-10 cm dishes. Each 10 cm dish was labeled as 100 cells per dish. At 14 days, the dishes were removed from the incubator, cells washed with PBS, and 3% crystal violet was added. No media change was required over the incubation. Cloning efficiency was estimated as the percentage of cells which generated clones from the total cell number/dish.

Other Embodiments

While the invention has been described in conjunction with the foregoing detailed description and examples, the foregoing description and examples are intended to illustrate and not to limit the scope of the invention, which is defined by the scope of the appended claims. Other aspects, advantages, and modifications are within the scope of the claims.

What is claimed is:

1. A method for isolating umbilical cord lining stem cells (ULSCs) from an umbilical cord, said method comprising
    a) obtaining the lining of an umbilical cord, wherein said lining is substantially free of blood, venous tissue, and arterial tissue; and
    b) culturing explants of said lining on a fibronectin-coated solid substrate in the presence of a low glucose growth medium for a period of time sufficient for said ULSCs to adhere to said fibronectin-coated solid substrate, said growth medium comprising 15% fetal bovine serum, a stabilized dipeptide of L-alanyl-L-glutamine, antibiotic, and a growth factor selected from the group consisting of basic fibroblast growth factor (bFGF), leukemia inhibitory factor (LIF), and epidermal growth factor (EGF).

2. The method of claim 1, said growth medium further comprising insulin, transferrin, selenium, and sodium pyruvate.

3. The method of claim 2, said growth medium further comprising putrescine.

4. The method of claim 3, said growth medium comprising bFGF, LIF, and EGF.

5. The method of claim 1, wherein said antibiotic is gentamycin.

6. The method of claim 1, wherein said antibiotic is penicillin and streptomycin.

7. The method of claim 1, wherein the upper surface of each said explant is in contact with a solid substrate.

8. The method of claim 1, said method further comprising washing said cells adhered to said fibronectin-coated solid substrate.

9. A composition for culturing umbilical cord lining stem cells (ULSCs), said composition comprising:
    a) a low glucose growth medium;
    b) 10% to 20% serum;
    c) 0.7 to 1.5% of a stabilized dipeptide of L-alanyl-L-glutamine;
    d) 1 to 100 ng/mL of a growth factor selected from the group consisting of basic fibroblast growth factor (bFGF), leukemia inhibitory factor (LIF), and epidermal growth factor (EGF); and
    e) 1 to 3% of an antibiotic.

10. The composition of claim 9, further comprising:
    f) 0.1 mg/mL to 100 mg/mL of insulin;
    g) 0.1 mg/mL to 100 mg/mL of transferrin;
    h) 0.1 µg/mL to 100 µg/mL of selenium; and
    i) 0.5 to 1.5% sodium pyruvate.

11. The composition of claim 10, further comprising 0.05 µg/mL to 100 µg/mL of putrescine.

12. The composition of claim 10, said composition comprising 15% serum; 1% of said stabilized dipeptide of L-alanyl-L-glutamine; 10 ng/mL of bFGF, 10 ng/mL of LIF; 1% of said antibiotic; 10 µg/mL of insulin; 0.55 mg/mL of transferrin; and 0.5 µg/mL of selenium.

13. The composition of claim 12, further comprising 10 µg/mL of putrescine and 10 ng/mL of EGF.

14. A composition comprising a purified population of ULSCs and a culture medium, wherein said culture medium comprises a low glucose growth medium; 10% to 20% serum; 0.7 to 1.5% of a stabilized dipeptide of L-alanyl-L-glutamine; 1 to 100 ng/mL of a growth factor selected from the group consisting of bFGF, LIF, and EGF; and 1 to 3% of an antibiotic, wherein said ULSCs are positive for CD105, CD106, CD90, CD73, SSEA-4, and STRO-1, and negative for CD45, CD34, CD19, and HLA-DR.

15. The composition of claim 14, wherein said culture medium further comprises 0.1 mg/mL to 100 mg/mL of insulin; 0.1 mg/mL to 100 mg/mL of transferrin; 0.1 µg/mL to 100 µg/mL of selenium; and 0.5 to 1.5% sodium pyruvate.

16. The composition of claim 15, wherein said culture medium further comprises 0.05 µg/mL to 100 µg/mL of putrescine and 1 ng/mL to 100 ng/mL of epidermal growth factor.

17. The composition of claim 14, wherein said composition further comprises a cryopreservative.

18. A purified population of umbilical cord lining stem cells, wherein said cells are positive for CD105, CD106, CD90, CD73, SSEA-4, and STRO-1, negative for CD45, CD34, CD19, and HLA-DR, express OCT4 and Nanog, and do not express Sox2, wherein said cells can undergo at least 60 population doubling in culture.

19. The purified population of ULSCs of claim 18, wherein said cells are capable Of differentiating into cells of mesodermal lineage.

20. The purified population of ULSCs of claim 19, wherein said cells are capable of differentiating into adipogenic cells, osteogenic cells, chondrogenic, and cardiogenic cells.

21. The purified population of ULSCs of claim 18, wherein said cells have undergone at least 70 population doublings in culture.

22. The purified population of ULSCs of claim 18, wherein said cells have undergone at least 90 population doublings in culture.

23. The purified population of ULSCs of claim 18, wherein said cells comprise an exogenous nucleic acid.

24. The purified population of ULSCs of claim 23, wherein said exogenous nucleic acid encodes a polypeptide.

25. The purified population of ULSCs of claim 18, wherein said cells are housed within a scaffold.

26. The purified population of ULSCs of claim 25, wherein said scaffold is biodegradable.

27. The purified population of ULSCs of claim 26, wherein said biodegradable scaffold is composed of collagen.

28. The purified population of ULSCs of claim 18, wherein said cells are capable Of differentiating into cells of the ectodermal lineage.

29. The purified population of ULSCs of claim 28, wherein said cells are capable Of differentiating into neurogenic cells.

30. A method for culturing a population of ULSCs, said method comprising obtaining a population of ULSCs from human umbilical cord, wherein said ULSCs are positive for CD105, CD106, CD90, CD73, SSEA-4, and STRO-1, negative for CD45, CD34, CD19, and HLA-DR, express OCT4 and Nanog, and do not express Sox2; and culturing said cells in the presence of a low glucose growth medium containing 10% to 20% serum; 0.7 to 1.5% of a stabilized dipeptide of L-alanyl-L-glutamine; 1 to 100 ng/mL of a growth factor selected from the group consisting of bFGF, LIF, and EGF; and 1 to 3% of an antibiotic, wherein said cells can undergo at least 60 population doubling in culture.

31. The method of claim 30, wherein said low glucose growth medium further comprises 0.1 mg/mL to 100 mg/mL of insulin; 0.1 mg/mL to 100 mg/mL of transferrin; 0.1 µg/mL to 100 µg/mL of selenium; and 0.5 to 1.5% sodium pyruvate.

32. The method of claim 31, wherein said culture medium further comprises 0.05 µg/mL to 100 µg/mL of putrescine and 1 ng/mL to 100 ng/mL of epidermal growth factor.

* * * * *

UNITED STATES PATENT AND TRADEMARK OFFICE
CERTIFICATE OF CORRECTION

PATENT NO. : 8,778,679 B2  Page 1 of 1
APPLICATION NO. : 13/668138
DATED : July 15, 2014
INVENTOR(S) : Francisco J. Silva and Rafael Gonzalez It is certified that error appears in the above-identified patent and that said Letters Patent is hereby corrected as shown below:

Column 2, Title Page, line 2 (Other Publications), please delete "Inuslin" and insert -- Insulin --, therefor,

IN THE CLAIMS:

Column 17, line 15 (Claim 18), please delete "doubling" and insert -- doublings --, therefor, Column 17, line 17 (Claim 19), please delete "Of" and insert -- of --, therefor, Column 18, line 8 (Claim 28), please delete "Of" and insert -- of --, therefor, Column 18, line 11 (Claim 29), please delete "Of" and insert -- of --, therefor, Column 18, line 23 (Claim 30), please delete "doubling" and insert -- doublings --, therefor.

Signed and Sealed this
Thirtieth Day of December, 2014

Michelle K. Lee
*Deputy Director of the United States Patent and Trademark Office*